United States Patent [19]
Forbes et al.

[11] Patent Number: 5,913,308
[45] Date of Patent: Jun. 22, 1999

[54] APPARATUS AND METHOD FOR DETERMINING RESPIRATORY EFFORT FROM MUSCLE TREMOR INFORMATION IN ECG SIGNALS

[75] Inventors: A. Dean Forbes, Palo Alto; Eric D. Helfenbein, Sunnyvale, both of Calif.

[73] Assignee: Hewlett-Packard Company, Palo Alto, Calif.

[21] Appl. No.: 08/769,557

[22] Filed: Dec. 19, 1996

[51] Int. Cl.$^6$ .................................................. A61B 5/0205
[52] U.S. Cl. ............................................................. 128/700
[58] Field of Search .................................. 128/670, 700, 128/733, 716, 723

[56] References Cited

PUBLICATIONS

Khaled, et al., "First Approach for Respiratory Monitoring by Amplitude Demodulation of the Electrocardiogram", Oct. 29–Nov. 1, 1992, *IEEE Engineering in Medicine and Biology 14th Annual Conference*, Paris, France, pp. 2535–2536.

Varanini, et al., "Adaptive Filtering of ECG Signal For Deriving Respiratory Activity", 1990, *IEEE Proceedings: Computers In Cardiology*, pp. 621–624.

McFarlane, "Lead Systems", 1989, *Comprehensive Electrocardiology: Theory and Practice in Health and Disease*, vol. 1, Pergamon Press, New York, pp. 315–351.

Pinciroli, et al, "Processing Electrocardiograms Towards Respiratory Signals", *IEEE Engineering In Medicine & Biology Society 10th Annual International Conference*, pp. 139–140.

Atwood, et al., "High–frequency Electrocardiography: An Evaluation of lead Placement and Measurements", Apr. 25, 1988, *Cardiac Catheterization Laboratory*, Long Beach VA Medical Center, pp. 733–739.

Amoore, et al., "Respiration and the ECG: A Study Using Body Surface Potential Maps", 1988, *J. Electrocardiology*, vol. 21(3), pp. 268–271.

Pinciroli, et al.,"Remarks and Experiments on the Construction of Respiratory Waveforms from Electrocardiographic Tracings", 1986, *Computers and Biochemical Research*, 19, pp. 391–409.

Moody, et al., "Derivation of Respiratory Signals From Multi–lead ECGs", Sep. 8–12, 1985, *Computers in Cardiology*, Linkoping, Sweden.

Pinciroli, et al., "Detection of Electrical Axis Variation For the Extraction of Respiratory Information", Sep. 8–12, 1985, *Computers in Cardiology*, Linkoping, Sweden.

*Primary Examiner*—Scott Getzow
*Attorney, Agent, or Firm*—Philip S. Yip

[57] ABSTRACT

An apparatus for determining the respiratory effort of a patient is disclosed. The apparatus includes a device for acquiring electrocardiographic (ECG) signal (e.g., conventional electrocardiogram (ECG) signal) that contains pure cardiac signal and respiratory muscle tremor (RMT) signal. The apparatus also includes a processor for processing the ECG signal. The processor includes a filter to filter the ECG signal for reducing the cardiac signal, a device for determining a waveform representing the magnitude of the oscillations in the filtered ECG signal, and a mechanism for smoothing spikes in the waveform. The resulting waveform is related to the respiratory muscle tremor, which is related to the respiratory effort. The estimation of the respiratory effort is derived entirely from the ECG signal.

17 Claims, 7 Drawing Sheets

APPARATUS AND METHOD FOR DETERMINING RESPIRATORY EFFORT FROM MUSCLE TREMOR INFORMATION IN ECG SIGNALS

FIELD OF THE INVENTION

The present invention is related to techniques for determining respiration in a patient and more particularly to apparatuses and methods for determining a waveform representing the respiratory effort of a patient.

BACKGROUND

Knowledge of a patient's respiratory status is important in many medical applications. For example, the respiration rate and/or phase of respiration (i.e., inspiration, expiration, end-expiration, etc.) of a patient can be used to assess a patient's clinical status or for diagnostic purposes. In addition, knowledge of respiratory phase can be used to assist cardiac imaging or diagnostic electrocardiogram (ECG) acquisition. Since respiration causes movement of the heart within the thorax, respiratory phase information can be used to gate image or ECG acquisition to a "quiet" or stable phase.

Respiratory information is traditionally determined by processing a respiration waveform obtained from a respiration sensor and/or specialized electronic hardware. One such sensor, a pneumotach, measures the flow of air with a tube through which the subject breathes. Mechanical sensors or strain gauges have been used to provide signals related to respiration by measuring the expansion and contraction of the chest with each breath. An electronic method traditionally used in conjunction with ECG monitoring involves measuring the electrical impedance through the torso to detect conductivity changes that occur as a result of respiration (mainly due to air in the lungs). A drawback of the above methods is that they require specialized hardware to obtain the respiratory signals.

ECG signals are routinely acquired and/or monitored in numerous applications. A number of methods have been developed to obtain the respiration waveform from an ECG waveform. Typically, these methods derive the respiratory information from the cardiac axis, the changes in ECG amplitude, or both the amplitude and R-R interval information in the ECG waveform. Such methods have a number of shortcomings.

The derivation of respiratory signals from ECG waveforms has been reported. The nature of the body surface ECG depends on the electrical activity of the heart, the physical geometry between the heart and the recording electrodes, and the conductivity of the torso. Respiration causes variation in the ECG since respiration affects heart-electrode geometry (due to motion of the heart resting on the diaphragm and chest expansion), conductivity (primarily due to filling of the lungs with air), and blood volumes in the ventricles. Studies have shown, however, that it is primarily the change in heart position which affects the ECG, with lung conductivity and ventricular volume changes having a minor influence (J. Amoore, Y. Rudy, J. Liebman, "Respiration and the ECG: A Study Using Body Surface Potential Maps," Journal of Electrocardiology 21 (3) 263–271, 1988).

In their work to create "virtual ECG leads" (representing the ECG signals which would come from electrodes fixed in position relative to the heart), Pinciroli et al. studied the electrical axis of the heart and whether variations in the electrical axis could be used to derive respiratory signals (F. Pinciroli, R. Rossi, L, Vergani, "Detection of Electrical Axis Variation for the Extraction of Respiratory Information," Computers in Cardiology, 1985). They defined the electrical axis as "the direction of prevalent development of the heart's cardiac activity" and that it is "defined by the straight line that best interpolates the ECG loops obtained from a pair of ECG traces according to the least square criterion." Pinciroli et al. computed the angle between this line and a reference direction for each beat, plotted the time series, and compared it to respiration curves obtained from a belt impedance meter. Moody employed a similar technique, but used the area of each normal QRS complex in each of two leads measured over a fixed time window to compute the mean axis (G. Moody, R. Mark, A. Zoccola, S. Mantaro, "Derivation of Respiratory Signals From Multi-Lead ECGs," Computers in Cardiology, 1985).

Techniques similar to the above for deriving respiration information from ECG signals have a number of shortcomings. For example, there are numerous methods for computing the mean electrical axis and the resulting angles and they are not equivalent in constructing a respiratory curve. Selection among sets of angles is not straightforward. Also, multiple orthogonal ECG leads are required, or a lead must be placed so that its axis is significantly different from the mean electrical axis to obtain a relatively large respiratory signal. Also, the respiratory curve can be adversely affected by ectopic beats, arrhythmias, or even a slow heart rate (due to undersampling).

Varanini et al. studied the use of an adaptive filter to derive the respiratory signal from a single ECG lead (M. Varanini, M. Emdin, et al., "Adaptive Filtering of ECG Signal for Deriving Respiratory Activity," Computers in Cardiology, 1990). They used the R-R interval and the R-wave amplitude time series extracted from the ECG signal as the inputs to the filter. The R-R interval series contains variations due to respiratory sinus arrhythmia (RSA), which is a modulation of the heart rate by the autonomic nervous system in response to respiration induced effects (e.g., baroreceptor influences). LMS (Least Mean Square) and RLS (Recursive Least Square) adaptive filtering methods were applied to obtain the estimate of the respiratory signal. However, such techniques suffer from convergence and stability problems, and tradeoffs must be made between the two. They also will be sensitive to undersampling problems if the cardiac to respiratory rate falls below a ratio of 2:1.

Khaled et al. described a simple amplitude demodulation technique to derive the respiratory signal from a single ECG lead (Z. Khaled, G. Farges, "First Approach for Respiratory Monitoring by Amplitude Demodulation of the Electrocardiogram," Proc. Annual Intl. Conf. IEEE Engineering in Medicine & Biology Soc., 1992). The ECG was first high-pass filtered to remove baseline wander. A peak detector then controlled a sample-and-hold circuit to hold a voltage level at the beat peak. This resulted in a step-wise waveform, which was considered to be the respiration waveform. In order for the Khaled et al. technique to work, the ECG lead must contain sufficient respiration-induced amplitude modulation. However, sufficient respiration-induced amplitude modulation may not always be present. Such a technique also suffers from a sensitivity to under-sampling due to the cardiac-respiration frequency ratio. What is needed is a simple, reliable technique for determining the respiratory effort of a patient using ordinary ECG signals.

SUMMARY

The present invention provides an apparatus for determining the respiratory effort of a patient. The apparatus includes a device for sensing body surface electrical potential (SEP) signals that include pure cardiac signals and respiratory muscle tremor (RMT) signals and a processor for processing the SEP signals. Typical conventional ECG signals are such SEP signals. Hereinafter, unless specified otherwise, the term "ECG signal" refers to the SEP signal. The processor includes a filter to filter the ECG signal and a device for determining an estimate-of-scale waveform representing the magnitude of the residual oscillations in the filtered ECG signal. The filtering of the ECG signal enhances the RMT signal in the filtered ECG signal compared to the unfiltered ECG signal. The estimate-of-scale waveform, after further processing to smooth the curvature of the waveform, provides a respiration waveform indicating the respiratory effort of the patient. The respiration waveform is derived entirely from the ECG signal.

The technique of the present invention can be advantageously used to sense and monitor the respiration of a patient. Since the ECG signals are used, there is no need for any additional device to inject or receive additional energy (other than receiving the ECG signals) into or from the patient as is done with the commonly used respiratory impedance method. Since the processing of ECG in accordance with the present invention can be done entirely in an electronic digital computer, the instrumentation on the patient need not be any more complex than the conventional ECG instrumentation. In fact, only one ECG lead is needed, so long as this lead provides respiratory muscle tremor signals. This method is called the tremor-derived-respiration (TDR) method herein.

For regular practice, the TDR method is not subjected to undersampling problems that may affect other techniques that compute respiratory samples one or two times per cardiac cycle. The TDR waveform can be computed using a sample rate equal to the sample rate of ECG. Because the muscle tremor signals originate from non-cardiac muscle, not the heart, TDR is independent of the cardiac events. As a result, the muscle tremor is not dependent on the cardiac rate, and our technique is not dependent on the heart rate to obtain adequate sampling. Furthermore, for the same reason, our technique is not adversely affected by the presence of ectopic beats and/or arrhythmias.

BRIEF DESCRIPTION OF THE DRAWINGS

The following figures are included to better illustrate the embodiments of the apparatus and technique of the present invention. In these figures, like numerals represent like features in the several views.

DETAILED DESCRIPTION OF THE INVENTION

In this invention, the respiratory effort is estimated from a patient's ECG signals (such as conventional ECG signals typically obtained with ECG electrodes on the torso of the patient) that contain both pure cardiac signals and signals from respiratory muscle tremor. This technique involves extracting muscle tremor potentials from the ECG signals and constructing a respiration waveform from the modulation of the tremor intensity, which is closely related to the respiratory effort exerted by the patient. The signals represented by such waveforms are referred to as tremor derived respiratory (TDR) signals. As used herein, "patient" can be used to refer to any mammalian individual, including a human, in whose respiratory effort a medical worker is interested.

Muscle Tremor due to Respiration

During inhalation, a person's diaphragm and intercostal muscles are activated. The electrical potentials generated by these muscles can be acquired through ECG electrodes placed on the chest. Such electrodes measure body surface electrical potentials (SEP) on the torso of the patient and the SEP signals will include both signals from these voluntary muscles and pure cardiac signals. These diaphragm and intercostal muscle signals are referred to as "muscle tremor noise," as they appear as a low-amplitude wide-spectrum waveform superimposed on the cardiac signals in the ECG. Usually the cardiac signals are the signals of interest and the muscle tremor signals are unwanted additive noise. In this invention, the muscle tremor is the desired signal. Methods of obtaining such ECG signals are known to those skilled in the art. See, e.g., MacFarlane, "Lead Systems," In MacFarlane and Lawire, ed., Comprehensive Electrocardiology—Theory and Practice in Health and Disease, Vol. 1, Pergamon Press, 1989, pp. 316–351.

Figure 1A:
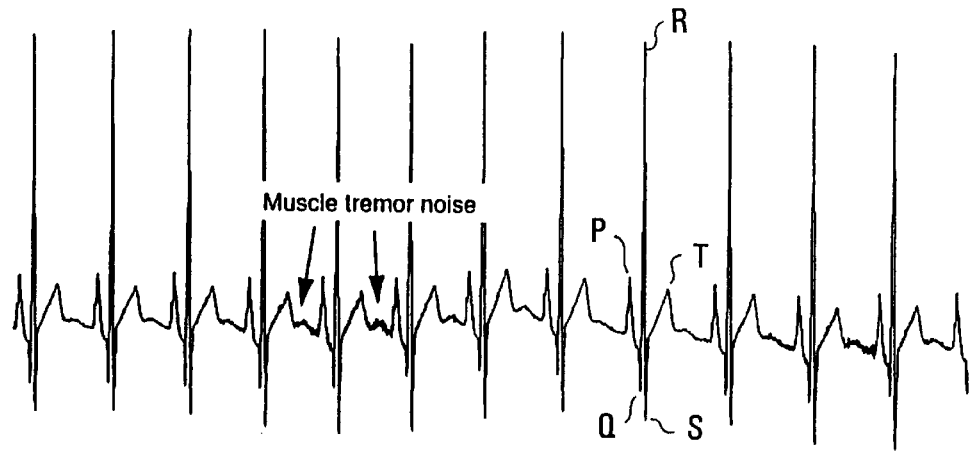
FIG. 1A shows an ECG waveform with muscle tremor for normal respiration (Y lead, 12 seconds).
Figure 1B:
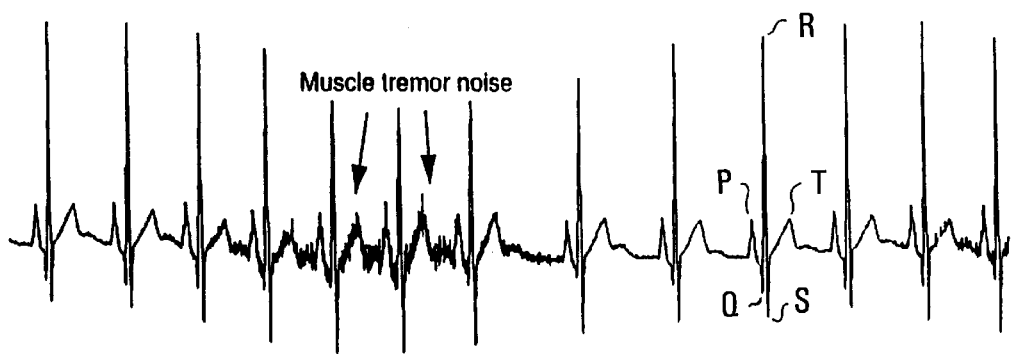
FIG. 1B shows an ECG waveform with muscle tremor during deep respiration (Y lead, 12 seconds).

Examples of ECG waveforms containing muscle tremor noise are shown in FIGS. 1A and 1B. The ECG data were taken using a standard orthogonal three dimensional XYZ lead system described by Atwood et al., "High-frequency electrocardiography: An evaluation of lead placement and measurements," Am. Heart J., 116(3): 733–739, 1988. As used herein, the term "waveform" refers to data or values that can be displayed in a display device such as a plotter, computer monitor, and the like, as well as a real graphical curve of these data or values displayed in a display device. The 1A and 1B waveforms were each obtained using a modified Y-lead for a period of 12 seconds. P, Q, R, S and T in these figures represent various complexes in the ECG and are known in the art. The data of FIG. 1A were recorded during normal respiration and the data of FIG. 1B were recorded during deep respiration. The muscle tremor potentials appear on the surface of the thorax as Gaussian white noise with a time-varying (cyclostationary) standard deviation closely related to respiratory effort.

As previously stated, ECG signals are acquired via leads attached to standard electrodes placed on the chest. In the above illustrative examples of FIGS. 1A and 1B, the signals were amplified, anti-alias filtered, and digitized at 2000 samples per second, a sample rate sufficiently high to represent the muscle tremor. The digitized samples can be stored for subsequent processing. If non-stationary electromagnetic interference (EMI) is present in the waveform (e.g., line frequency interference and/or its harmonics), EMI filtering techniques can be used to remove it prior to further processing. For example, the cosine trend filtering technique (application Ser. No. 08/624,194, HP Patent Application Docket #10951188, entitled: "Robust Time-Diversity Filter for Removing Electromagnetic Interference", Forbes et al.), or other commonly used filtering (e.g., notch filtering) techniques can be employed for this purpose.

PREFERRED EMBODIMENTS

Figure 2:
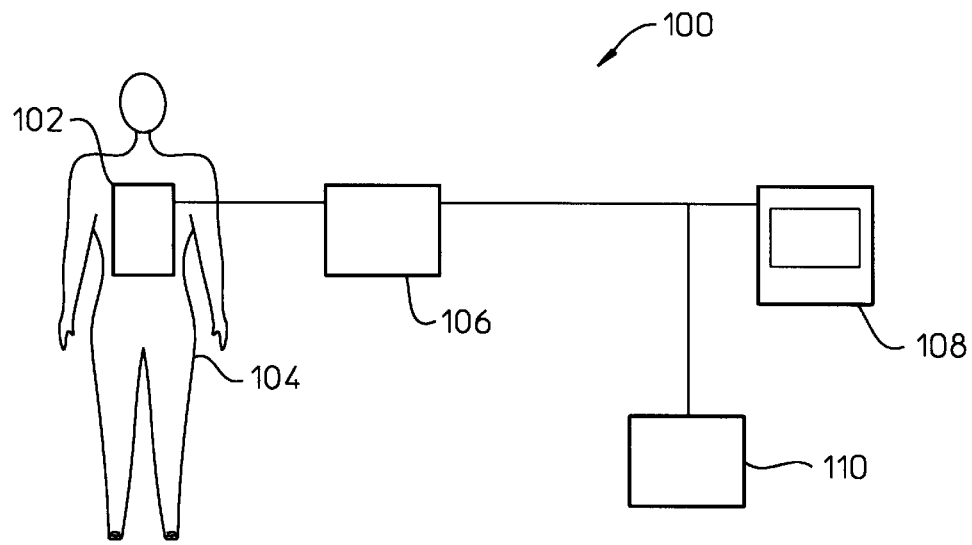
FIG. 2 is a schematic representation of an embodiment of the apparatus of the present invention.

FIG. 2 shows a schematic example of the present invention. The apparatus 100 of the present invention includes a device 102 for acquiring ECG signals from a patient 104. Typically this device 102 will be a sensor device including electrodes, wires, amplifier, etc., for producing electrical signals suitable for downstream processing to obtain information on respiration. It is also contemplated that the ECG signals can be imported from a remote location or from a storage device. The apparatus 100 further includes a processor 106 for processing the ECG signals and a display device 108 for displaying the respiration waveform after processing the ECG signals.

Figure 3:
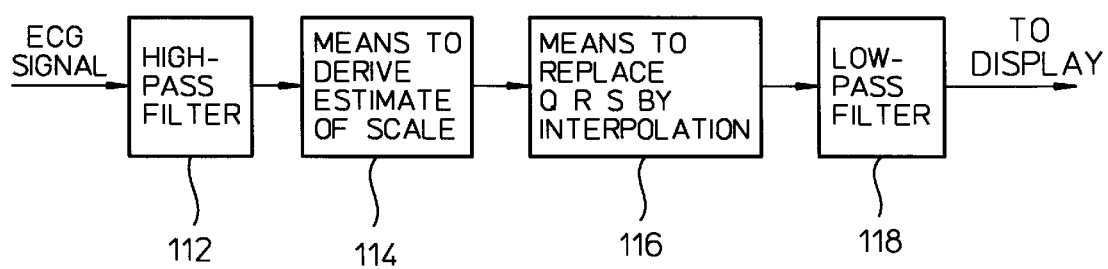
FIG. 3 is a schematic representation of a processor in the apparatus of FIG. 2.

FIG. 3 shows in block diagram the further details of the processor 106 in apparatus 100. The processor 106 includes a high-pass filter 112 which filters the ECG signals coming from the sensor device 102. If desired, the ECG signals can be filtered with an appropriate device to reduce electromagnetic interference (EMI) before the high-pass filter 112. The high-passed signals are then processed by a mechanism 114 that derives estimate-of-scale data from the high-passed signals. The estimate-of-scale data are then further processed by a data-replacement mechanism 116 which replaces the data corresponding to the QRS complexes of the ECG waveform with interpolation to cover the QRS complexes. The resulting data are then filtered with a low-pass filter 118 to smooth the curve of the resulting waveform. This waveform is called the "respiration waveform" herein and represents the respiratory effort of the patient and can be displayed in a display device 108 or stored in a storage device 110, e.g., the random-access-memory of a computer, a hard disk, floppy disk, compact disk, magnetic tape, and the like. The respiration waveform (data) can also be used for other purposes, e.g., in the processing of of other signals or images from the patient, or in the control or monitoring of the patient's physiological functions.

Figure 4:
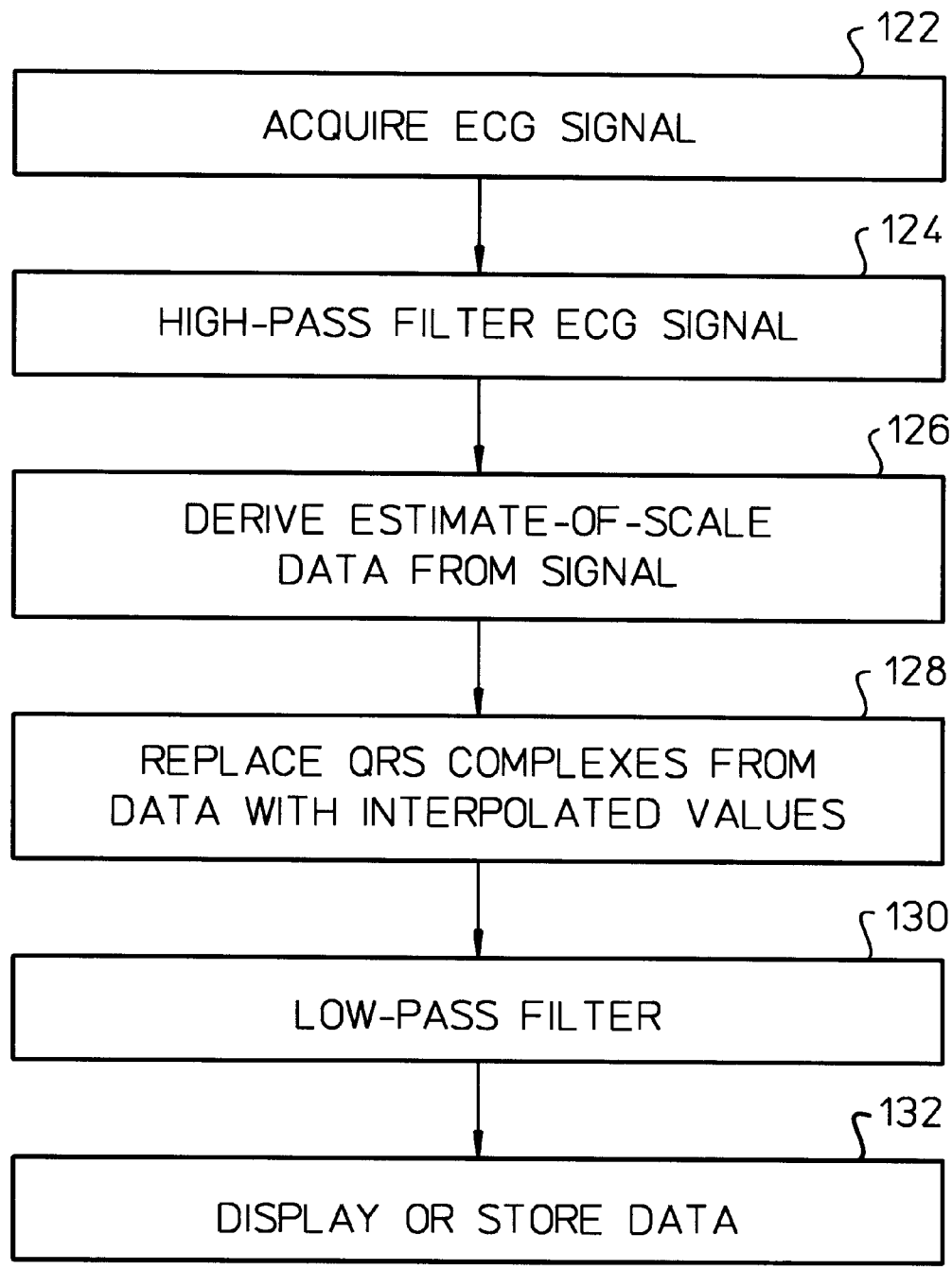
FIG. 4 is a flow diagram showing the steps in a process of the present invention.

FIG. 4 shows a flow diagram representing the process of obtaining a respiration waveform according to the present invention. ECG signals containing muscle tremor signals are sensed from a patient using commonly known ECG techniques by electrodes on the patients body (step 122). This step can include amplifying the signals from the electrodes and filtering out noise, such as electromagnetic interference, and the like. The sensed ECG signals are then high-pass filtered (step 124). The high-pass filtered signals are then processed to derive estimate-of-scale data so that when displayed the estimate-of-scale data can be represented by a curve showing the magnitude of oscillation (step 126). The QRS complexes of the data are then removed and the missing data are replaced by interpolated values (step 128). The data are then low-pass filtered (step 130) and displayed in a display device, such as a CRT, monitor, plotter, printer, etc. Alternatively, the data can be stored in a memory device for analysis, review, processing, or display later.

High-Pass Filter

The acquired ECG signal (e.g., EMI filtered ECG signal) is high-pass filtered to separate the high-frequency muscle tremor from as much of the cardiac signal as possible. This removes the low-frequency components of the ECG as well as any DC offset and/or low frequency baseline wander ("electrode drift"). By filtering, the muscle tremor signal is "enhanced" relative to the cardiac signal in the sense that the filtering removes more of the cardiac signal than the muscle tremor signal. High-frequency ECG components will remain, however, and will be dealt with in a later step. After high-pass filtering, the signal will be zero mean. The choice of the frequency cutoff for the high-pass filter will depend on the sample rate of the data and on the cutoff of the data acquisition anti-aliasing filter (i.e., the filter cutoff should be substantially below that of the low-pass anti-aliasing filter), which are apparent to a skilled person in the art, with knowledge of the present invention. For example, we used a FIR high-pass filter with a cutoff of 250 Hz on our 2000 samples per second data.

Figure 5:
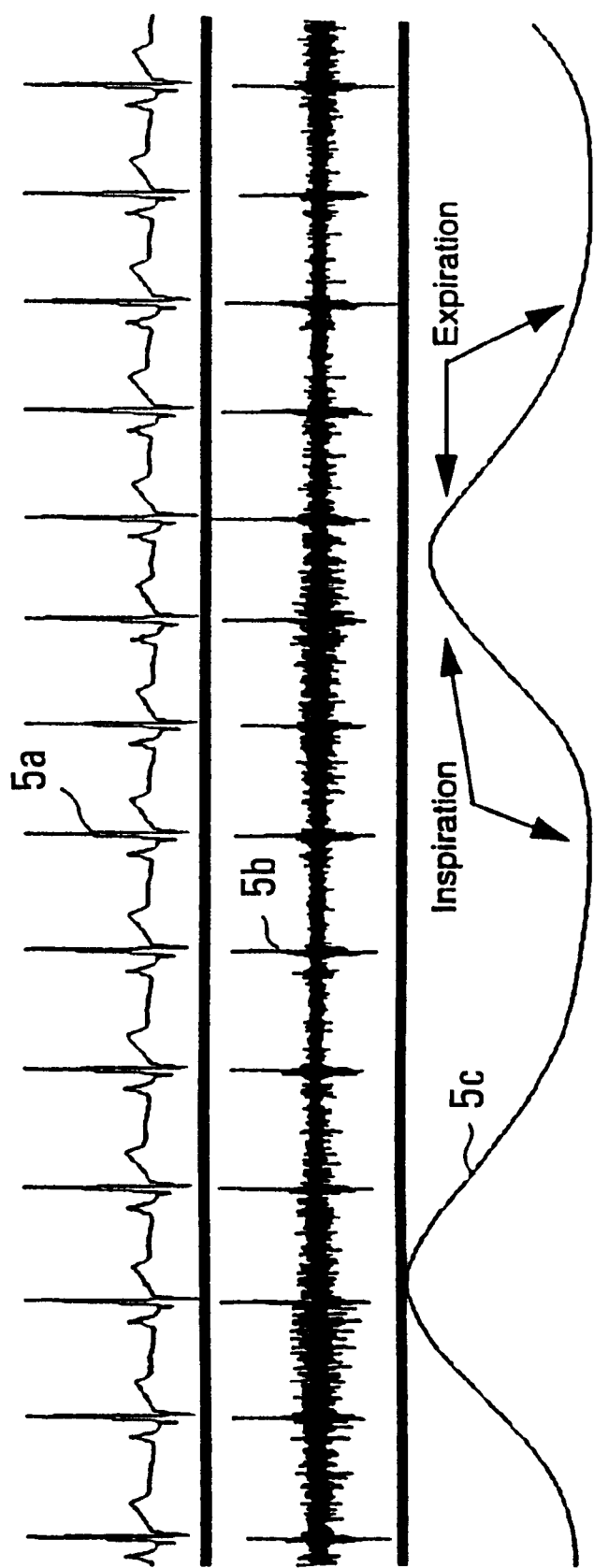
FIG. 5 are graphs showing the ECG signal, the high-pass-filtered ECG signal, and the corresponding respiration impedance signal.

In FIG. 5, the top trace 5a shows an ECG signal (Y lead, 12 seconds). The middle trace 5b in FIG. 5 shows an ECG waveform that has been high-pass filtered at 250 Hz cutoff to accentuate the muscle tremor. For comparison, the bottom trace 5c shows the corresponding respiratory impedance on the patient obtained by using the respiratory impedance method, which is known in the art. Ignoring (for FIG. 5) the high-frequency components of the cardiac cycle which survive the high-pass filtering and which should eventually be removed (i.e., the spikes occurring at each beat location), we see that the intensity of the muscle tremor is at its greatest during inspiration and is at its lowest at end-expiration.

Computing Short-Term Tremor Estimate-of-Scale Values in a Sliding Window

As can be seen in curve 5b of FIG. 5, the magnitude of oscillation of the high-pass filtered signal is related to the respiratory muscle tremor. By separating the tremor signal from the cardiac signal and examining the magnitude of oscillation we can compute the tremor-derived respiratory (TDR) signal, which is correlated with the phases of respiration. The magnitude of oscillation is indicative of the muscle tremor magnitude. The intensity of the muscle tremor can be quantified by computing an estimate-of-scale, i.e., an estimate related to the magnitude of oscillation of the muscle tremor. For example, in FIG. 5 we see that the magnitude of oscillation is larger near the end of inspiration, which indicates the magnitude of oscillation can show the phasic characteristics of the patient's respiratory effort.

We derive an estimate-of-scale waveform to represent the patient's respiratory phases. One way to derive an estimate-of-scale waveform is to measure the time-varying standard deviation (SD) of the (band-passed, zero-mean Gaussian) tremor waveform, which is equivalent to the RMS amplitude. Since the SD cannot be computed instantaneously (i.e. using only one sample), a collection of adjacent samples falling within a sliding (i.e., moving), fixed-duration window can be used to estimate the tremor SD in a local region. In choosing the duration of this window, there is a tradeoff between estimation accuracy and over-sensitivity to spurious variations. As an illustrative example, we have chosen 50 milliseconds as a nominal value for the short-term window width. The center of the window is initially placed to correspond with the first sample point of the data. The sum of the squared values for each data point in the window is computed. This sum is then divided by the number of data points spanned by the window, and the square root is taken of this value. The result is herein referred to as the root-mean-square (RMS) amplitude of the high-passed tremor signal over the short-term window. Other methods of estimating scale can be used, such as summing the absolute values of the data in the sliding window, and the like. Such methods will be apparent to those skilled in the art.

Figure 6:
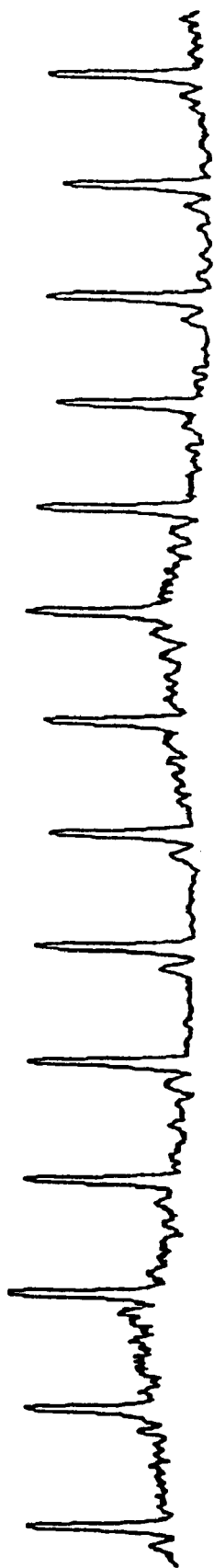
FIG. 6 is a graph of the root mean squared (RMS) signal of the high-pass-filtered signal of FIG. 5.

The RMS value is saved as the first sample of a new waveform we refer to as the "RMS waveform." The sliding window is then advanced by one data sample, and the process is repeated until the end of the data is reached. At each step, the computed RMS value is stored in the RMS waveform at the point corresponding to the center of the sliding window. An example RMS waveform (obtained from the data of FIG. 5) is shown in FIG. 6. The tremor RMS waveform created in this example has a sample rate equal to that of the ECG waveform. Since the relevant frequency components of the respiratory signal are much lower than those of the ECG, as an alternative, a much lower sample rate can be employed to represent the respiratory signal. Such a reduction in sample rate will reduce computational requirements and can be accomplished in this step by advancing the center of the moving window by more than one sample at each iteration.

Replacing QRS Complexes with Interpolation Values

In this example, some high frequency components of each heartbeat (i.e., the QRS wave or QRS complex) remain in the signal after the high pass filter. This residual energy appears as a spike in the RMS waveform at times corresponding to the QRS complex in the ECG signal, as shown in FIG. 6 and the middle trace of FIG. 7. This residual energy is due to cardiac activity and not from muscle tremor. Although the RMS waveform can be further processed to obtain the respiration waveform without removing the QRS complexes, preferably, this QRS artifact is removed. We remove it by replacing each QRS complex with a series of interpolated samples (e.g., linear interpolation) following a line segment connecting a point before each spike to a point after the spike.

Figure 7:
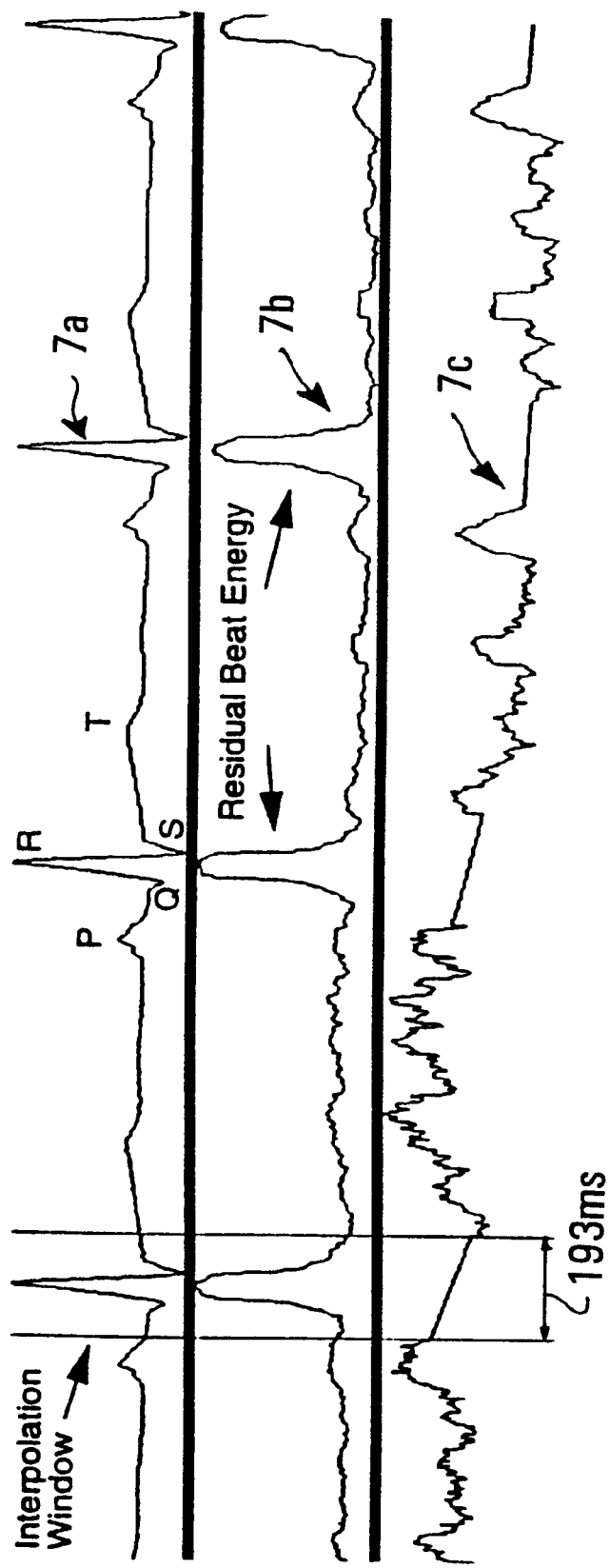
FIG. 7 are graphs of the ECG signal, RMS signal, and amplified RMS signal after replacing QRS complexes with interpolation values.

To implement this scheme, the location of each beat is determined by processing the original ECG waveform with a QRS detection algorithm. Many known QRS detection algorithms can be employed for this purpose by one skilled in the art. Once a beat location is determined, a point before the beat and a point after the beat are picked on the RMS waveform. The two points can be determined by using a fixed duration before and after the peak of the QRS complex (e.g., 200 msec, total), or by dynamically identifying the start and end of each QRS complex. Using the fixed duration approach will require less intensive computing than otherwise, but may allow excess artifact to remain, especially if wide, ectopic beats are present. However, minor errors in this procedure will have a minimal effect on the derived respiration waveform because the QRS duration is relatively short compared to the duration of each respiratory cycle. Once the two points spanning the QRS complex are identified, the data on the waveform between these two points are replaced with a series of interpolated (e.g., linear interpolation) sample values. In FIG. 7, trace 7c shows an example signal after the replacement of QRS artifact with interpolation values. The Y-lead ECG signal (top trace 7a) and RMS signal (middle trace 7b) corresponding to trace 7c are shown for comparison. In this example, the first QRS shown has a duration computed to be 193 msec, and is replaced with interpolated values over this interval. Energy due to atrial depolarization, i.e., P-waves, may still be present, but is usually insignificant. If the P-waves are large, the interpolated region can be extended to remove the P-wave artifact.

Low-Pass Filter to Smooth the Estimate-of-Scale Waveform

Figure 8:
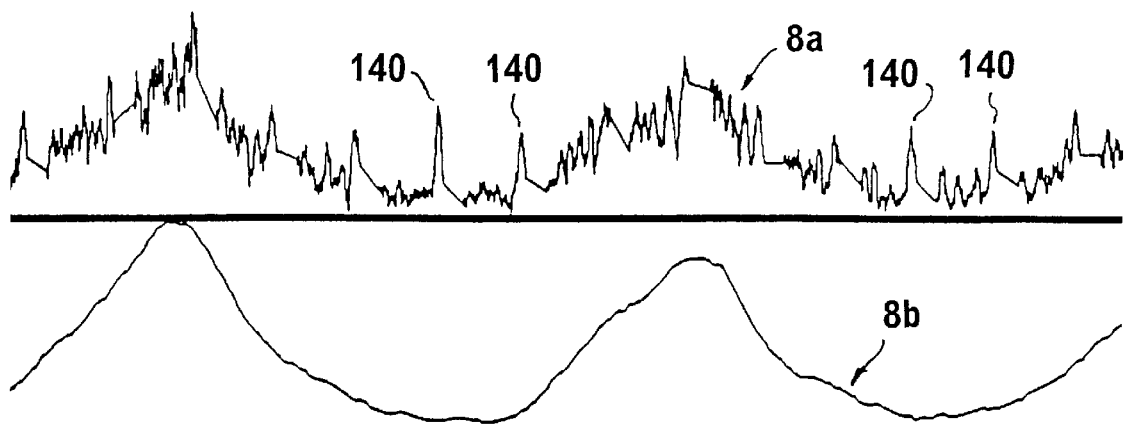
FIG. 8 are graphs showing, in more detail, the RMS signal after replacing QRS complexes with interpolation values and showing the RMS signal after further low-pass filtering, i.e., the muscle tremor derived respiration (TDR) waveform.

The top trace 8a of FIG. 8 shows another example of a RMS waveform, which has the QRS artifact removed and replaced by linear interpolation. In this example, spikes 140, due to atrial depolarization, are still present. Also, at this point, the RMS waveform still may contain a large amount of high frequency variation, due to the high-frequency nature of the tremor wave, and due to the interpolation employed to remove the QRS spikes. Because the respiratory rate is generally slower than the heart rate (i.e., cardiac frequency), we smooth this waveform with a low-pass filter. Preferably, the low pass filter substantially filters out frequencies higher than the cardiac frequency. Also, since the interpolation occurs at the cardiac frequency, (i.e., done at each beat), a dynamic low-pass filter with its first zero dynamically placed at the cardiac frequency is preferably used. An example for such dynamic filters is the PETA (Physiological Event Time Averaging) filter (U.S. Pat. No. 5,511,554, Helfenbein et al., *"Real-Time Artifact Removal From Waveforms Using a Dynamic Filter Having a Fixed Delay,"* HP Docket No. 1094498-1, which is incorporated by reference herein). We process the beat-free RMS waveform with the PETA filter, using the previously determined beat locations as the event input to the filter. Using such a low-pass filter with its first zero at the cardiac frequency further removes residual cardiac power as well as the sudden disturbances introduced by the interpolation process occurring at each beat. Since the PETA filter employs a "boxcar" moving average window, its low-pass nature effectively removes the unwanted high-frequency components while allowing the low-frequency respiratory signal to pass. The resulting waveform, after the PETA filter, is shown in the lower trace 8b of FIG. 8.

Figure 9:
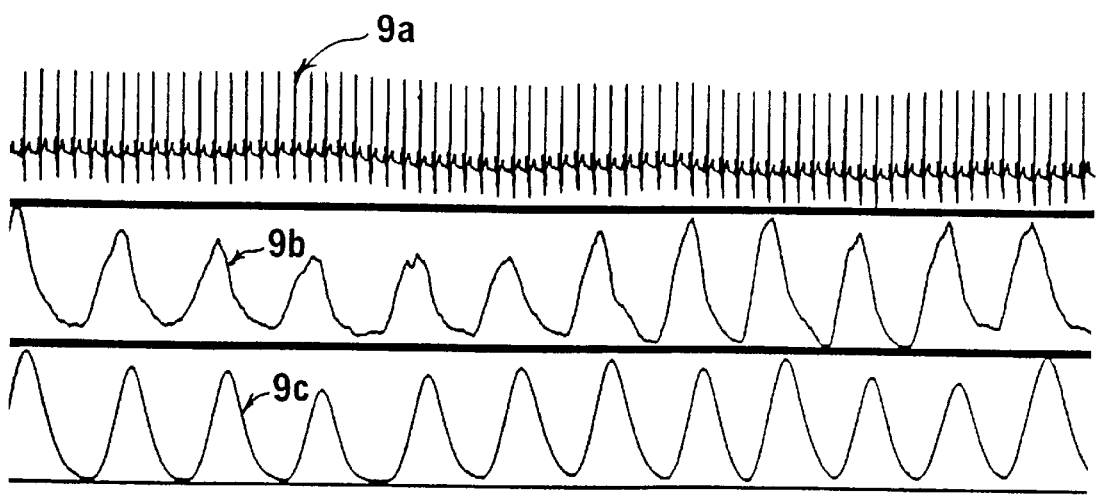
FIG. 9 are graphs showing ECG signal, the TDR waveform, and a respiratory impedance waveform.

We have compared the TDR waveform to the respiration signal obtained by impedance measurement, and found them to be well correlated. An example of normal respiration is shown in FIG. 9. Trace 9a shows the ECG signal and is shown for comparison purposes. The TDR waveform 9b matches the impedance waveform 9c quite well and can be used to represent the respiratory effort of a patient. Here, the impedance waveform (trace 9c) usually lags the TDR (trace 9b) by approximately *600* msec. This delay is believed to be due to the diaphragm and intercostal muscles being excited prior to physical motion. This delay should not have significant practical effect in typical respiration monitoring.

It is to be understood that the processor 106 can be an electronic computer that can perform the functions of the high pass filter 112, mechanism for estimating scale 114, mechanism for replacing data 116, and low pass filter 118. The computer can perform computation sequentially and do these functions one at a time. Alternatively, one skilled in the art will be able to implement separately wired electronic circuits, as well as microprocessor-based circuits that perform the above functions involving high-pass filtering, QRS removal, interpolation, low-pass filtering, etc. It is contemplated that a computer program be written to direct a computer to process ECG signals in accordance with the present invention and that such a program can be stored in a storage medium such as hard disks, floppy disks, compact disks, tapes, and the like. Such a storage medium will contain memory that holds codes executable by the computer to perform the functions of means or mechanisms 112, 114, 116, and 118, as well as other functions desired.

Although the preferred embodiment of the present invention has been described and illustrated in detail, it is to be understood that a person skilled in the art can make modifications within the scope of the invention.

What is claimed is:

1. An apparatus for determining the respiratory effort of a patient, comprising:

(a) means for acquiring electrocardiographic (ECG) signal that includes pure cardiac signal and respiratory muscle tremor (RMT) signal; and (b) processor means for processing the ECG signal, the processor means including:

(i) filter means for filtering the ECG signal to result in filtered ECG signal such that the prominence of the RMT signal is enhanced in the filtered ECG signal; and (ii) means for determining an estimate-of-scale waveform representing the magnitude of the oscillations in the filtered ECG signal, thereby obtaining a respiration waveform from the magnitude of the RMT such that the respiration waveform is determined entirely from the ECG signal.

2. The apparatus according to claim 1 wherein the filter means uses a high-pass filter to remove low frequency components of the ECG signal.

3. The apparatus according to claim 1 wherein the processor means is adapted to determine magnitude of oscillation of the filtered ECG signal to determine the estimate-of-scale waveform.

4. The apparatus according to claim 3 wherein the processor means is adapted to obtain a root means square (RMS) average of the filtered ECG signal to determine the estimate-of-scale waveform.

5. The apparatus according to claim 3 wherein the processor means further comprises a means for removing data corresponding to QRS waves in the ECG signal and interpolating to bridge data before and after the QRS waves.

6. The apparatus according to claim 1 wherein the processor means is adapted to determine the cardiac interval and the cardiac frequency determined from the ECG signal, the processor means including a dynamic low-pass filter having a moving average window with a width equal to the cardiac interval and having a first zero at about the cardiac frequency.

7. The apparatus according to claim 1 wherein the filter means includes a high-pass filter to remove low frequency components of the ECG signal, the means for determining an estimate-of-scale waveform is adapted to obtain the estimate-of-scale waveform of the filtered ECG signal by estimating the magnitude of oscillation of the high-pass-filtered data, the processor means further including means for replacing data corresponding to QRS waves in the ECG signal with interpolation and including a low pass filter to smooth the estimate-of-scale waveform after replacing the QRS waves.

8. The apparatus according to claim 1 wherein the means for acquiring ECG signal comprises electrodes and the apparatus further comprises a display means for displaying the respiration waveform or a storage means for storing the respiration waveform.

9. A method for using an apparatus that analyses for the respiratory effort of a patient, the apparatus having a filter and an estimator of scale, the method comprising:

(a) acquiring electrocardiographic (ECG) signal of the patient, which includes respiratory muscle tremor (RMT) signal;

(b) filtering the ECG signal with the filter to result in a filtered ECG signal such that the prominence of the RMT signal is enhanced in the filtered ECG signal; and (c) using the estimator of scale to obtain an estimate-of-scale waveform of the magnitude of oscillations of the filtered ECG signal to determine a respiration waveform from the magnitude of the RMT signal, such that the respiration waveform is determined entirely from the ECG signal.

10. The method according to claim 9 wherein the filtering step comprises high-pass filtering the ECG signal to remove low frequency components therefrom.

11. The method according to claim 10 further comprising a step of removing data corresponding to QRS complexes in the ECG signal and interpolating to bridge data before and after the QRS complexes.

12. The method according to claim 9 wherein the step of obtaining the estimate-of-scale waveform comprises determining magnitude of oscillation of the filtered ECG signal.

13. The method according to claim 12 wherein the step of obtaining the estimate-of-scale waveform of the filtered ECG signal comprises replacing portions of the waveform corresponding to QRS portions in the ECG signal with interpolated values.

14. The method according to claim 13 wherein the step of determining the estimate-of-scale waveform of the filtered ECG signal further comprises, after replacing and interpolation, smoothing the resulting waveform by substantially filtering out frequencies higher than the cardiac frequency.

15. The method according to claim 13 wherein the step of determining the estimate-of-scale waveform further comprises, after replacing and interpolation, filtering the resulting data with a dynamic low-pass filter having a first zero at about the cardiac frequency determined from the ECG signal to smooth the waveform.

16. A method for using an apparatus that analyses for the respiratory effort of a patient, the apparatus having a high-pass filter and an estimator of scale, the method comprising:

(a) acquiring electrocardiographic (ECG) signal of the patient, which includes respiratory muscle tremor (RMT) signal;

(b) filtering the ECG signal with the high-pass filter to result in a filtered ECG signal such that the prominence of the RMT signal is enhanced in the filtered ECG signal; and (c) using the estimator of scale to obtain an estimate-of-scale waveform of the magnitude of oscillations of the filtered ECG signal, to replace data corresponding to QRS portions of the ECG signal with interpolation values and to filter the resulting waveform with a moving window low-pass filter with a first zero at about a cardiac frequency determined from the raw ECG signal to smooth the resulting waveform such that the resulting respiration waveform is determined entirely from the ECG signal.

17. A program storage medium readable by a computer, tangibly embodying a program of instruction including code means executable by the computer to perform method steps for determining the respiratory effort of a patient, the program storage medium comprising:

a memory device having code means which includes:

(a) code means for filtering electrocardiographic (ECG) signal that includes pure cardiac signal and respiratory muscle tremor (RMT) signal to result in a filtered ECG signal such that the prominence of the RMT signal is enhanced in the filtered ECG signal;

(b) code means for determining an estimate-of-scale waveform of the magnitude of oscillations of the filtered ECG signal; and (c) code means for removing the interfering effect of QRS portions of the filtered ECG signal from the estimate-of-scale waveform to determine a respiration waveform of the patient from the magnitude of the RMT signal, such that the respiration waveform is determined entirely from ECG signal.

* * * * *